United States Patent [19]

Hijiya et al.

[11] Patent Number: 5,723,651

[45] Date of Patent: Mar. 3, 1998

[54] PROCESS FOR PRODUCING α-L-ASPARTYLDIPEPTIDE AMIDE DERIVATIVES

[75] Inventors: Toyoto Hijiya; Tadashi Takemoto; Ryoichiro Nakamura; Yusuki Amino; Naoko Sugiyama, all of Kawasaki, Japan

[73] Assignee: Ajinomoto Co., Inc., Tokyo, Japan

[21] Appl. No.: 579,975

[22] Filed: Dec. 28, 1995

[30] Foreign Application Priority Data

Dec. 28, 1994 [JP] Japan .................................. 6-327094
Aug. 24, 1995 [JP] Japan .................................. 7-215940

[51] Int. Cl.⁶ .................................................. C07C 229/00
[52] U.S. Cl. ........................... 560/169; 560/41; 560/142; 560/144; 560/145; 549/76; 549/493; 549/434; 546/329; 546/333; 426/548; 558/414
[58] Field of Search ............................ 564/123; 560/41, 560/142, 144, 145, 169; 562/561, 565, 450; 426/598; 546/329, 333; 549/76, 434, 493; 558/414

[56] References Cited

U.S. PATENT DOCUMENTS 4,411,925  10/1983  Brennan et al. ..................... 426/548

FOREIGN PATENT DOCUMENTS

| 0 034 876 | 9/1981 | European Pat. Off. . |
| 0 099 960 | 2/1984 | European Pat. Off. . |
| 0 149 582 | 7/1985 | European Pat. Off. . |
| WO 94/00028 | 1/1994 | WIPO . |

OTHER PUBLICATIONS

The Chemical Synthesis of Peptides, pp. 49–51, 1991, John Jones, "Activation and Coupling of Amino Acid Derivatives".

Chemical Abstracts, vol. 108, No. 13, AN 112959z, Mar. 28, 1988.

*Primary Examiner*—Shailendra Kumar
*Attorney, Agent, or Firm*—Oblon, Spivak, McClelland, Maier & Neustadt, P.C.

[57] ABSTRACT

An economical process for producing α-L-aspartyldipeptide amide derivatives useful as sweeteners, by using amino protecting groups which can be removed by hydrolysis under acidic conditions, resulting in conversion of a β-carboxyl acid ester to a carboxylic acid.

9 Claims, No Drawings

PROCESS FOR PRODUCING α-L-ASPARTYLDIPEPTIDE AMIDE DERIVATIVES

BACKGROUND OF THE INVENTION

Field of the Invention

This invention relates to a process of producing of α-L-aspartyldipeptide amides useful as sweeteners, etc.

BACKGROUND OF THE INVENTION

α-L-aspartyl-D-amino acid-N-(S)-α-alkylbenzylamide, included in the invention, is an artificial sweetener disclosed in U.S. Pat. No. 5,286,509, incorporated herein by reference. The patent discloses a process of producing this compound by condensing N-benzyloxycarbonyl-L-aspartic acid-β-benzylester which has the amino group and β-carboxyl group of the L-aspartic protected acid with D-amino acid-N-(S)-α-alkylbenzylamide using dicyclohexylcarbodiimide; then the benzyloxycarbonyl group and benzyl group are removed by catalytic reduction to obtain the target compound. This method requires the use of expensive dicyclohexylcarbodiimide in its industrial production. In addition, the target compound may contain a small amount of dicyclohexylurea derived from the reaction of dicyclohexylcarbodiimide, resulting in a product of inferior quality.

The patent states that N-benzyloxycarbonyl-L-aspartic acid anhydride or N-formyl-L-aspartic acid anhydride can be used in the previous method; however, no specific methods or conditions are disclosed and β-L-aspartyl-D-amino acid amide derivatives are produced as byproducts in addition to or rather than the target α-L-aspartyl-D-amino acid amide derivatives when the amino group of the D-amino acid amide attacks the carbonyl carbon of the carboxyl group at β-position of aspartic acid. The β by-products need to be removed, and reduced production yields of the target compound are obtained.

OBJECTS OF THE INVENTION

One object of the present invention is to provide an economical process of producing α-L-aspartyldipeptide amide derivatives.

DETAILED DESCRIPTION OF THE INVENTION

The above object has been attained by a process where an aspartic acid derivative of formula (1) is mixed with alkyl chloroformate to produce a mixed anhydride, and then mixed with an amino acid amide derivative of formula (2), following which the resulting compound is hydrolyzed under acidic conditions to remove the amino protecting group on aspartic acid and to convert the β-carboxylic acid ester to carboxylic acid.

Formula (1) aspartic acid derivatives have the following structure:

(1)

wherein $R_1$ is an alkyl or alkoxy group with 1 to 4 carbon atoms or an aromatic group with 6 to 10 carbon atoms; $R_2$ is an alkyl group with 1 to 4 carbon atoms or an aromatic group with 6 to 10 carbon atoms; $R_3$ is an alkyl group with 1 to 4 carbon atoms or a benzyl group; A is a protonated tertiaryamine or protonated dicyclohexylamine or an alkaline metal.

Formula (2) amino acid amide derivatives have the formula:

(2)

wherein $R_1$ is a linear or branched alkyl group with 1 to 6 carbon atoms or an alkoxymethyl group (e.g., $CH_3CH_2$—O—$CH_2$—) with 2 to 7 carbon atoms; $R_2$ is a benzyl group, a cyclohexyl group, a cyclohexylmethyl group (e.g., $C_6H_{11}$—$CH_2$—), a phenyl group, or a phenyl group with a substituent in its 2-, 3- or 4-position selected from F, Cl, Br, I, a hydroxyl group, an alkoxy group with 1 to 6 carbon atoms, a cyano group, a nitro group, an acetyl group, an amino group, an acetyl amino group, or $R_2$ is a phenyl group with a methylenedioxy group, a trimethylene group, or a tetramethylene group in its 2,3- or 3,4-position, or $R_2$ is a 2-, 3- or 4-pyridyl group, a 2- or 3-furyl group, or a 2- or 3-thienyl group; the configuration of C* is (S) or (RS) when $R_1$ is an alkyl group; (R), (S) or (RS) when $R_1$ is an alkoxymethyl group. When $R_1$ is an alkyl group and $R_2$ is a benzyl group, a cyclohexyl group, a cyclohexylmethyl group, or phenyl group X is a D-α-amino acid residue or a DL-α-amino acid residue selected from D-norleucine, D-leucine, D-isoieucine, D-alloisoleucine, D-threonine, D-O-methylthreonine, D-allothreonine, D-O-methylallothreonine, D-or DL-furylglycine, or a cyclic or non-cyclic α,α-dialkyl amino acid residue with 3 to 6 carbon atoms. When 1) $R_1$ is an alkyl group and $R_2$ is a phenyl group with a substituent in its 2-, 3- or 4-position selected from F, Cl, Br, I, a hydroxyl group, an alkoxy group with 1 to 6 carbon atoms, a cyano group, a nitro group, an acetyl group, an amino group, an acetylamino group, or a phenyl group with a methylenedioxy group, a trimethylene group or a tetramethylene group in its 2,3- or 3,4-position, or a 2-, 3- or 4-pyridyl group, a 2- or 3-furyl group, or a 2- or 3-thienyl group or 2) when $R_1$ is an alkoxymethyl group X is a D-α-amino acid residue or a DL-α-amino acid residue selected from D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-phenylglycine, D- or DL-furylglycine, or a cyclic or non-cyclic α,α-dialkylamino acid residue with 3 to 6 carbon atoms. L-aspartic acid (L-Asp) and X are α-bonded.

The aspartic acid derivative of formula (1) can be produced by mixing L-aspartic acid β-alkyl ester with an "A" base and β-diketones or acetoacetic acid esters as amino protecting groups in an appropriate solvent. The appropriate solvents include water, alcohols such as methanol and ethanol, ethers such as tetrahydrofuran and 1,4-dioxane, nitriles such as acetonitrile, dimethylformamide, dimethylsulfoxide and mixtures thereof.

L-aspartic acid β-alkylesters can be easily obtained by treating L-aspartic acid with thionyl chloride in the corresponding alkyl alcohol (H. Schwarz et.al., J. Am. Chem. Soc., 79, 5697 (1957)) or in alkyl alcohol containing hydrogen halide (D. W. Coleman et. al., J. Chem. Soc., 1951, 2294) etc.

The "A" bases include tertiary amines such as triethylamine, tributylamine, trioctylamine and N-methylmorpholine, secondary amines such as dicyclohexylamine, etc. and preferably having a bulky substituent and weak nucleophilicity, and inorganic bases consisting of alkaline metals such as sodium hydroxide, potassium hydroxide, and sodium carbonate. Tertiary amines such as tributylamines and trioctylamines are especially preferred because of their slurry properties in the reaction mixture of the next process.

Amino-protecting groups include acetoacetic acid esters such as methyl acetoacetate and ethyl acetoacetate, and β-diketones such as acetylacetone and benzoylacetone.

The aspartic acid derivative of formula (1) produced by the invention process (i.e., mixing said three substances) coexists with water which will be produced during reaction. A protic solvent such as water and alcohol interferes with the reaction, so it needs to be removed in an appropriate manner before the reaction with alkyl chloroformate begins in the next process step. To distill off water and alcohol, the reaction solution can be concentrated; when they solidify in the reaction solution, the solid can be separated from the liquid by filtering or other methods.

To produce a mixed anhydride from the compound of formula (1) and alkyl chloroformate, the compound of formula (1) may be dissolved or suspended by an aprotic solvent, then alkyl chloroformate can be added to obtain a mixed anhydride.

The aprotic solvent includes aromatic hydrocarbons such as benzene and toluene, acetic acid esters such as ethyl acetate and butyl acetate, ketones such as acetone and methylethylketone, hydrocarbon halides such as dichloromethane and chloroform, and ethers such as tetrahydrofuran and dioxane. Overall, aromatic hydrocarbons and acetic acid esters are preferred because of their liquid properties in the reaction mixture and the deprotecting process.

It is desirable for the reaction to take place at a low temperature to suppress side reactions. The temperatures that bring the best yields are $\leq 5°$ C., preferably $\leq 0°$ C. and ideally $\leq -0°$ C.

It is economical that the mixing molar ratio of the compound of formula (1) and alkyl chloroformate is equal to 1 (the same molar amounts), however, the molar ratio may range from 0.6 to 1.5.

Alkyl chloroformates include methyl chloroformate, ethyl chloroformate, isobutyl chloroformate, and benzyl chloroformate. The alkyl group can thus be linear, branched, cyclic or aromatic and may have from 1–10 or more carbon atoms.

By mixing the reaction solution containing the mixed anhydride resulting from the formula (1) compound with an alkylchloroformate with the amino acid amide derivative of formula (2), protected α-L-aspartyldipeptide-amide derivatives of formula (5) are obtained easily:

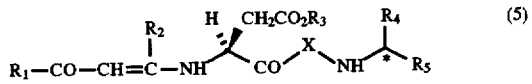

where $R_1$, $R_2$ and $R_3$ are as defined above for formula (1) and $R_4$ and $R_5$ correspond to $R_1$ and $R_2$ in formula (2) above. X is as in formula (2) above. Preferably in formula (5), $R_1$ is an alkyl or alkoxy group with 1 to 4 carbon atoms or aromatic group with 6 to 10 carbon atoms; $R_2$ is an alkyl group with 1 to 4 carbon atoms or aromatic group with 6 to 10 carbon atoms; $R_3$ is an alkyl group with 1 to 4 carbon atoms or a benzyl group; $R_4$ is an alkyl group with 1 to 6 carbon atoms or alkoxymethyl group with 2 to 7 carbon atoms; $R_5$ is a benzyl, cyclohexyl, cyclohexylmethyl or phenyl group; or a phenyl group with a substituent in its 2-, 3- or 4-position selected from the group comprising of F, Cl, Br, I, a hydroxy group, an alkoxy group with 1 to 6 carbon atoms, a cyano group, a nitro group, an acetyl group, an amino group and an acetylamino group; or $R_5$ is a phenyl group with methylenedioxy group, trimethylene group or tetramethylene group in its 2,3- or 3,4 position, or $R_5$ is a 3- or 4-pyridyl, 2- or 3-furyl, or 2- or 3-thienyl group. The configuration of C* is (S) or (RS) when $R_4$ is an alkyl group; (R), (S) or (RS) when $R_4$ is an alkoxymethyl group.

When $R_4$ is an alkyl group and $R_5$ is a benzyl group, a cyclohexyl group, a cyclohexylmethyl group, or a phenyl group X is a D-α-amino acid residue or a DL-α amino acid residue selected from the group comprising D-norleucine, D-leucine, D-isoleucine, D-alloisoleucine, D-threonine, D-O-methylthreonine, D-allothreonine, D-O-methylallothreonine, D- or DL-furylglycine, or cyclic or non-cyclic α,α-dialkyl amino acid residue with 3 to 6 carbon atoms. When 1) $R_1$ is an alkyl group and when $R_5$ is a phenyl group with a substituent in its 2-, 3- or 4-position selected among the group comprising F, Cl, Br, I, hydroxyl, alkoxy groups with 1 to 6 carbon atoms, cyano, nitro, acetyl, amino, acetylamino groups, or when $R_5$ is a phenyl group with methylenedioxy group, trimethylene group or tetramethylene groups in its 2,3- or 3,4-position, or when $R_5$ is a 2-, 3- or a 4-pyridyl group, a 2- or 3-furyl group, or a 2- or 3-thienyl group, or 2) when $R_4$ is an alkoxymethyl group X is a D-αamino acid residue or a DL-amino acid residue selected from the group comprising D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-phenylglycine, D- or DL-furylglycine, or a cyclic or non-cyclic α,α-dialkylamino acid residue with 3 to 6 carbon atoms. L-Asp and X are α-bonded.

The amino acid amide derivative of this invention can be obtained by removing the protective group from N-benzyloxycarbonyl or N-tert-butoxycarbonyl amino acid amide derivatives, as disclosed in U.S. Pat. No. 5,286,509; it can also be obtained by using the organic layer obtained initially by condensing the mixed anhydride of amino acid derivatives of formula (3) with amine derivatives of formula (4), then exposing the product to acidic water to obtain an aqueous solution containing amino acid amide derivatives for extraction with organic solvent under alkaline conditions. Formula (3) is as follows:

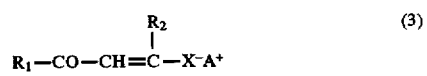

wherein $R_1$ is an alkyl or alkoxy group with 1 to 4 carbon atoms or an aromatic group with 6 to 10 carbon atoms; $R_2$ is an alkyl group with 1 to 4 carbon atoms or an aromatic group with 6 to 10 carbon atoms; X is a D-α-amino acid residue or a DL-α-amino acid residue selected among the group comprising D-alanine, D-α-amino butyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine or D-phenylglycine, D- or DL-furylglycine, or a cyclic or non-cyclic α,α-dialkyl amino acid residue with 3 to 6 carbon atoms.

"A" represents protonated tertiaryamine, dicyclohexylamine, or an alkaline metal; formula (4) is as follows:

wherein $R_1$ is an alkyl group with 1 to 6 carbon atoms or an alkoxymethyl group with 2 to 7 carbon atoms; $R_2$ is a benzyl group, a cyclohexyl group, a cyclohexylmethyl group, a phenyl group, or a phenyl group with a substituent in its 2-, 3- or 4-position selected from F, Cl, Br, I, a hydroxyl group, an alkoxy group with 1 to 6 carbon atoms, a cyano group, a nitro group, an acetyl group, an amino group, an acetylamino group, or a phenyl group with a methylenedioxy group, a trimethylene group, a tetramethylene group in its 2,3- or 3,4-position, or a 2-, 3- or 4-pyridyl group, a 2- or 3-furyl group, or a 2- or 3-thienyl group; the configuration of C* is (S) or (RS) when $R_1$ is an alkyl group; (R), (S) or (RS) when $R_1$ is an alkoxymethyl group.

In this process, conditions for the mixed anhydride reaction and condensation reactions remain the same as described previously: the same sub-materials such as alkyl chloroformate and tertiaryamine, and the temperature are used both for condensing amine derivatives of formula (4) with amino acid derivatives and for the resulting condensed compound with aspartic acid component. This means that the method is very advantageous industrially due to the common use of identical storage tanks and reaction vessels.

In the resulting mixture, protected α-L-aspartyldipeptide amide derivatives exist. The procedure to obtain the target α-L-aspartyldipeptide amide derivative by removing the protecting group is as follows: add mineral acid aqueous solution such as diluted hydrochloric acid to the reaction mixture to expose it under acidic conditions at room temperature for from 30 minutes to several hours. In this way, the amino protecting group can be readily cleaved, resulting in α-L-aspartyldipeptide amide β-alkylester of formula (6). When a solvent in which the compound of formula (5) is poorly soluble is employed, this substance may be present as a crystal or in the form of a solid. In such a case, a solid/liquid separation procedure such as filtration is conducted to obtain the solid to which then dilute hydrochloric acid is added to yield the substance corresponding to formula (6). Formula (6) is as follows:

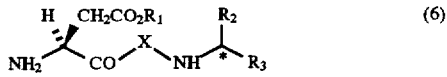

wherein $R_1$ is an alkyl group with 1 to 4 carbon atoms or a benzyl group; $R_2$ is an alkyl group with 1 to 6 carbon atoms, or alkoxymethyl group with 2 to 7 carbon atoms, $R_3$ is a benzyl, cyclohexyl cyclohexylmethyl, phenyl group, or a phenyl group with a substituent in its 2-, 3- or 4-position selected from F, Cl, Br, I, a hydroxyl group, an alkoxy group with 1 to 6 carbon atoms, cyano, nitro, acetyl, amino, acetyl amino groups, or a phenyl group with a methylenedioxy, trimethylene, or tetramethylene group in its 2,3- or 3,4- position, or a 2,3- or 4-pyridyl, 2- or 3-furyl group, or 2 - or 3-thienyl group; the configuration of C* is (S) or (RS) when $R_2$ is an alkyl group; (R), (S) or (RS) when $R_2$ is an alkoxymethyl group.

When $R_2$ is an alkyl group and $R_3$ is a benzyl, cyclohexyl, a cyclohexylmethyl, or phenyl group X is a D-α-amino acid residue or a DL-α amino acid residue selected from the group comprising D-norleucine, D-leucine, D-isoleucine, D-alloisoleucine, D-threonine, D-O-methylthreonine, D-allothreonine, D-O-methylallothreonine, D-or DL-furylglycine, or cyclic or non-cyclic α,α-dialkyl amino acid residue with 3 to 6 carbon atoms. When 1) $R_2$ is an alkyl group, and $R_3$ is a phenyl group with a substituent in its 2-, 3- or 4-position selected among the group comprising F, Cl, Br, I, a hydroxyl group, an alkoxy group with 1 to 6 carbon atoms, a cyano group, a nitro group, an acetyl group, an amino group, an acetylamino group, or a phenyl group with a methylenedioxy group, a trimethylene group or a tetramethylene group in its 2, 3- or 3, 4-position, or 2, 3- or a 4-pyridyl group, a 2- or 3-furyl group, or a 2- or 3-thienyl group, or 2) when $R_2$ is an alkoxymethy group X is a D-α-amino acid residue or a DL-α-amino acid residue selected from the group comprising D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-phenylglycine, D-or DL-furylglycine, or a cyclic or non-cyclic α,α-dialkylamino acid residue with 3 to 6 carbon atoms. L-Asp and X are α-bonded.

The substance of formula (6) is hydrolyzed under acidic conditions to convert the β-ester in aspartic acid into carboxylic acid and produce the objective α-L-aspartyldipeptide amide derivatives. This reaction requires more severe process conditions than simply removing the amino protecting group. The required acid concentration should be equivalent to from 1N to 6N hydrochloric acid and the temperature is from room temperature to 80° C. The process time is between 30 minutes and 24 hours to hydrolyze esters without cleaving the amide bond of the target substance. For example, higher acid concentration can be combined with a relatively low temperature and shorter time.

When the benzyl ester is in the β-position, the ester group can be removed by catalytic reduction: remove the amino protecting group in the acid solution, then add a catalyst such as Pd-Carbon to achieve the conversion into carboxylic acid while stirring under hydrogen atmosphere. Then, after removal of the catalyst by filtration, the mixture is neutralized to obtain the target α-L-aspartyldipeptide amide derivatives.

Removal of the amino protecting group and hydrolysis of the esters can take place at the same time. It is preferable that the compounds of formula (5) are separated from the reaction solution by concentrating or filtering when using solvents such as ethyl acetate which can easily be hydrolyzed.

The resulting compound of formula (5) can be exposed to the ester hydrolysis conditions to remove the amino protecting group at the same time. When using unhydrolyzable solvents such as toluene, the condensation reaction solution can be exposed to hydrolytic conditions.

The resulting acidic solution containing α-L-aspartyldipeptide amide derivatives can be neutralized with bases such as sodium hydroxide and then crystallization can be controlled by concentration or cooling to obtain the objective α-L-aspartyldipeptide amide derivatives in crystal form.

EXAMPLES

The following examples will further describe the invention in particular detail. The invention is not limited to the examples. The HPLC conditions were as follows. Column: Inertsil ODS-2, 6Φ×150 mm; eluent: 0.1M $KH_2PO_4$ (pH3.0) /MeCN=80/20 (V/V); flow rate: 1 ml/min; temperature: room temperature; detection: UV (210 nm).

Example 1

1.27 g (6.90 mmol) of L-aspartic acid β-methyl ester hydrochloride, 0.80 g (6.9 mmol) of methyl acetoacetate, 4.88 g (13.8 mmol) of trioctyl amine were added to 20 ml of methanol (Solution I); Solution I was refluxed for three hours, then concentrated under reduced pressure. 27 ml of ethyl acetate was added to the residue (syrup) and was cooled to below −10° C. while stirring, and 10 ml of ethyl acetate solution containing 0.66 ml (6.9 mmol) of ethyl chloroformate was added while maintaining the temperature of the reaction solution at −11° C. to −12° C. 20 minutes later, 15 ml of ethyl acetate solution containing 1.37 g (5.85 mmol) of D-valine-N-(S)-α-ethylbenzylamide was added to the reaction solution while maintaining the temperature at −13° C. to −17° C. The reaction mixture was warmed to room temperature and 20 ml of 1N-HCl was added and stirred for one hour at room temperature. After the solution was separated into layers, the ethyl acetate layer was extracted twice with diluted hydrochloric acid. The aqueous layer was collected, HPLC analyzed, and measured 1.81 g (4.97 mmol) of α-L-aspartyl-D-valine-N-(S)-α-ethylbenzylamide β-methyl ester. The yield was 85.0%.

The aqueous layer was concentrated, 12 ml of 2N-HCl was added to the residue and kept at 60° C. for five hours. The hydrolyzed solution was HPLC analyzed and measured 1.55 g (4.45 mmol) of α-L-aspartyl-D-valine-N-(S)-α-ethylbenzylamide. The yield was 89.4%.

The hydrolyzed solution pH was adjusted to pH 6 with 25% NaOH, and the resulting slurry was stirred at 5° C. overnight and filtered at reduced pressure. The resulting α-L-aspartyl-D-valine-N-(S)-α-ethylbenzylamide crystals were rinsed with a small amount of water and dried at reduced pressure. The amount was 1.42 g. The crystallization yield was 91.4%.

Example 2

5.85 g (50.0 mmol) of D-valine, 5.81 g (50.0 mmol) of methyl acetoacetate and 9.05 g (50.0 mmol) of dicyclohexylamine were added to 50 ml of methanol (solution II). Solution II was heated to reflux for three hours and concentrated at reduced pressure. 165 ml of ethyl acetate and 0.48 g (4.7 mmol) of N-methylmorpholine were added to the residue and stirred while cooling, and 60 ml of ethyl acetate solution containing 6.18 ml (4.72 mmol) of isobutyl chloroformate was added while maintaining temperature at −17° C. to −20° C. 20 minutes later, 100 ml of ethyl acetate solution containing 5.42 g (40.1 mmol) of (S)-α-ethylbenzylamine was also added to the mixture while maintaining the temperature as it was. The mixture was warmed to the room temperature and then filtered to remove precipitated dicyclohexylamine hydrochloride crystals and 100 ml of 1N HCl was added to the filtrate. The mixture was stirred at the room temperature for ninety minutes and was separated into layers. The aqueous layer was adjusted to pH11 with 1N-NaOH and extracted with approximately 200 ml of ethyl acetate. The resulting 226 ml of ethyl acetate layer contained 6.63 g (28.3 mmol) of D-valine-N-(S)-α-ethylbenzylamide. The yield was 70.5%.

3.06 g (16.7 mmol) of L-aspartic acid-β-methyl ester hydrochloride, 2.25 g (19.4 mmol) of methyl acetoacetate and 6.51 g (35.9 mmol) of dichlorohexylamine were added to 30 ml of methanol, then refluxed while heating for three hours; the reaction mixture was concentrated at reduced pressure.

Ethyl acetate was added to the residue and then filtered to remove precipitated dicyclohexylamine hydrochloride. The filtrate was concentrated to obtain 8.38 g of syrup-like residue. 50 ml of ethyl acetate and 0.85 g (8.4 mmol) of N-methylmorpholine were added to the residue, and the resulting mixture was cooled as described above, and ethyl acetate solution containing 2.17 ml (16.7 mmol) of isobutyl chloroformate was added. 20 minutes later, about 35 ml of the concentrate made from 120 ml of the ethyl acetate layer (containing 15 mmol of D-valine-N-(S)-α-ethylbenzyiamide) was added.

The temperature was raised to the room temperature and filtered at reduced pressure to obtain deposited crystals. The crystals were hydrolyzed with 100 ml of 0.5N HCl at room temperature for two hours and then filtered to remove precipitated dicyclohexylamine hydrochloride and the filtrate was HPLC analyzed and measured 3.60 g (9.91 mmol, yield: 66.0%) of α-L-aspartyl-D-valine-N-(S)-α-ethylbenzylamide β-methylester and 0.116 g (0.332 mmol, yield: 2.2%) of α-L-aspartyl-D-valine-N-(S)-α-ethylbenzylamide. The aqueous layer, obtained by mixing the mother liquor with diluted hydrochloric acid and separating into layers, was HPLC analyzed and measured 0.545 g (1.50 mmol, yield: 10.0%) of α-L-aspartyl-D-valine-N-(S)-α-ethylbenzylamide methyl ester and 26 mg (0.073 mmol; yield: 0.5%) of α-L-aspartyl-D-valine-N-(S)-α-ethylbenzylamide. The total condensation yield was 78.7%. The above two hydrolyzed solutions were put together and concentrated, and 200 ml of 2N-HCl were added to the residue and kept at 60° C. for four hours, and then 3.58 g (10.26 mmol, yield: 86.9%) of α-L-aspartyl-D-valine-N-(S)-α-ethylbenzyl amide was measured.

Example 3

1.84 g (10. Ommol) of L-aspartic acid β-methyl ester hydrochloride, 1.00 g (10. Ommol) of acetylacetone and 3.63 g (20.0 mmol) of dicyclohexylamine were added to 40 ml of methanol (Solution III); Solution III was refluxed while heating for three hours and concentrated at reduced pressure. 50 ml of ethyl acetate was added to the resulting syrup-like residue and was cooled to <−10° C. and stirred; 11 ml of ethyl acetate solution containing 0.96 m. (10 mmol) of ethyl chloroformate was added while maintaining the reaction solution temperature at −11° C. to −12° C. 20 minutes later, 45 ml of ethyl acetate solution containing 1.91 g (9.27 mmol) of D-α-aminobutyric acid-N-(S)-α-methyl benzyl amide was added while maintaining the reaction solution temperature at −13° C. to −17° C. The solution was warmed to the room temperature and them filtered to remove dicyclohexylamine hydrochloride and the filtrate was concentrated; acetonitrile and 40 ml of 2N-HCl were added to the residue, and then heated at 60° C. for four hours. The resulting solution was HPLC analyzed and measured 1.79 g (5.58 mmol) of α-L-aspartyl-D-α-aminobutyric acid-N-(S)-α-methylbenzylamide. The yield was 60.6%.

Example 4

1.02 g (5.00 mmol) of L-aspartic acid β-benzyl ester, 0.63 ml (5. Ommol) of ethyl acetoacetate and 0.909 g (5.00 mmol) of dicyclohexylamine were added to 30 ml of methanol (Solution IV); Solution IV was stirred at the room temperature overnight and concentrated at reduced pressure. 22 ml of ethyl acetate and 0.3 ml of triethylamine were added to the residue, and the mixture was stirred while cooling below −10° C.; 7 ml of ethyl acetate solution containing 0.47 ml (4.94 mmol) of ethyl chloroformate was added while maintaining the reaction solution temperature at −20°±5° C. 30 minutes later, approximately 6 ml of the concentrate made of 34 ml of the ethyl acetate layer of Example 2 containing 4.22 mmol of (D-valine-N-(S)-α-ethylbenzyl amide) was added to the reaction solution while maintaining the temperature at −20°±3° C. The mixture was warmed to room temperature and then filtered to remove dicyclohexylamine hydrochloride and 11 ml of 1N-HCL was added to the filtrate, and the mixture was stirred at room temperature for one hour and concentrated. 40 ml of acetic acid was added to the syrup-like residue, and then 0.36 g of 10% Pd-C was added, and the mixture was stirred for three days under hydrogen atomsphere for catalytic reduction. The mother liquor, after catalyst removal, was HPLC analyzed and measured 0.592 g (1.70 mmol) of α-L-aspartyl-D-valine-N-(S)-α-ethylbenzyl amide. The yield was 40.2%.

Example 5

1.52 g (13.0 mmol) of D-valine, 1.51 g (13.0 mmol) of methyl acetoacetate, 2.36 g (13.0 mmol) of dicyclohexylamine were added to 13 ml of methanol; the solution was refluxed while heating for three hours and concentrated at reduced pressure. 45 ml of ethyl acetate and 0.13 g (1.3 mmol) of N-methylmorpholine were added to the residue and stirred and cooled (Solution V);15 ml of ethyl acetate solution containing 1.71 ml (13.0 mmol) of isobutyl chloroformate was added to Solution V while maintaining the temperature at −15° C. to −17° C. 20 minutes later, 25 ml of ethyl acetate solution containing 1.59 g (10.5 mmol) of (R)-α-methoxymethylbenzylamine was added while maintaining the same temperature. The solution was warmed to room temperature, and then, filtered to remove precipitated dicyclohexylamine hydrochloride. 25 ml of 1N-HCL was added to the filtrate and the solution was then stirred for ninety minutes at room temperature to separate into layers. The resulting aqueous layer was adjusted to pH11 with 1N NaOH and the mixture was extracted with approximately 50 ml of ethyl acetate. The resulting ethyl acetate layer was dried with anhydrous magnesium sulfate; the mixture was filtered and the filtrate was concentrated at reduced pressure, and then it was dried to obtain 2.16 g (8.63 mmol) of D-valine-N-(R)-α-methoxymethylbenzylamide in form of clear light yellow syrup. The yield was 82.2%.

1.84 g (10.0 mmol) of L-aspartic acid β-methyl ester hydrochloride, 1.16 g (10.0 mmol) of methyl acetoacetate and 3.63 g (20.0 mmol) of dicyclohexylamine were added to 18 ml of methanol; then the mixture was refluxed while heating for three hours and concentrated at reduced pressure. Ethyl acetate was added to the residue and then filtered to remove precipitated dicyclohexylamine hydrochloride. The filtrate was concentrated to obtain 4.74 g of syrup-like residue. 30 ml of ethyl acetate and 0.51 g (5.0 mmol) of N-methylmorpholine were added to the residue and was cooled as described above, and ethyl acetate solution containing 1.31 ml (10.0 mmol) of isobutyl chloroformate was added. 20 minutes later, the solution made by dissolving 2.13 g (8.52 mmol) of the D-valine-N-(R)-α-methoxymethylbenzylamide into 20 ml of ethyl acetate was added to the mixture. The solution was warmed to the room temperature and was concentrated at reduced pressure to distill ethyl acetate off. Acetonitrile and 200 ml of 2N HCl were added to the residue and heated at 60° C. for twenty hours. The solution was HPLC analyzed and measured 2.49 g (6.81 mmol) of α-L-aspartyl-D-valine-N-(R)-α-methoxymethylbenzyl amide. The yield was 79.9%.

The hydrolyzed solution was adjusted to pH6 with 25% NaOH and was concentrated at reduced pressure; the resulting slurry was ice cooled and filtered at reduced pressure. The resulting α-L-aspartyl-D-valine-N-(R)-α-methoxymethylbenzylamide crystals were rinsed with a small amount of water, ethyl acetate and chloroform and was dried under reduced pressure. The gained amount was 2.00 g. The crystallization yield was 80.3%.

Example 6

1.47 g (8.0 mmol) of L-aspartic acid-β-methyl ester hydrochloride, 0.93 g (8.0 mmol) of methyl acetoacetate and 5.66 g (16.0 mmol) of trioctyl amine were added to 25 ml of methanol (Solution VI); Solution VI was refluxed while heating for three hours and was concentrated at reduced pressure. 30 ml of ethyl acetate was added to the resulting syrup-like residue and was stirred while cooling to −10° C.; 15 ml of ethyl acetate solution containing 0.77 ml (8.0 mmol) of ethyl chloroformate was added to the mixture while maintaining the temperature at −11° C. to −12° C. 20 minutes later, 20 ml of ethyl acetate solution containing 1.79 g (6.78 mmol) of D-valine-N-(R)-α-ethoxymethylbenzylamide was added while maintaining the temperature at −13° C. to −17° C. The solution was warmed to room temperature and 25 ml of 1N HCl was added to the reaction solution and the solution was stirred at room temperature for one hour.

After layers were separated, the ethyl acetate layer was extracted twice with diluted hydrochloric acid solution. The aqueous layer was concentrated and 15 ml of 2N HCl was added to the residue, and the mixture was heated at 60 C. for eight hours. The hydrolyzed solution was HPLC analyzed and measured 2.25 g (5.94 mmol) of α-L-aspartyl-D-valine-N-(R)-α-ethoxymethylbenzylamide. The yield was 87.6%.

The hydrolyzed solution was adjusted to pH6 with 25% NaOH and the resulting slurry was stirred at 5° C. overnight, and then filtered at reduced pressure. The resulting α-L-aspartyl-D-valine-N-(R)-α-ethoxymethylbenzylamide crystals were rinsed with a small amount of water and dried under reduced pressure. The gained amount was 2.01 g. The crystallization yield was 89.4%.

Example 7

1.84 g (10.0 mmol) of L-aspartic acid β-methyl ester hydrochloride, 1.00 g (10.0 mmol) of acetylacetone and 3.63 g (20.0 mmol) of dicyclohexylamine were added to 40 ml of methanol (Solution VII); Solution VII was refluxed while heating for three hours and concentrated at reduced pressure. 50 ml of ethyl acetate was added to the resulting syrup-like residue and stirred while cooling below −10° C.; 15 ml of ethyl acetate solution containing 0.96 ml (10.0 mmol) of ethyl chloroformate was added while maintaining the temperature at −11° C. to −12° C. 20 minutes later, 40 ml of ethyl acetate solution containing 2.15 g (9.11 mmol) of D-α-aminobutyric acid-N-(R)-α-methoxymethylbenzyl amide was added to the reaction solution while maintaining the temperature at −13° C. to −17° C. The solution temperature was raised to the room temperature and the mixture was filtered to remove dicyclohexylamine hydrochloride. The filtrate was concentrated; acetonitrile and 40 ml of 2N HCl were added to the residue and the mixture was heated at 60° C. for five hours. The solution was HPLC analyzed and measured 2.16 g (6.16 mmol) of α-L-aspartyl-D-α-aminobutyric acid-N-(R)-α-methoxymethylbenzylamide. The yield was 67.6%.

Example 8

2.04 g (10.0 mmol) of L-aspartic acid β-benzylester, 1.26 ml (10.0 mmol) of ethyl acetoacetate and 1.82 g (10.0 mmol) of dicyclohexylamine were added to 50 ml of methanol (Solution VIII); Solution VIII was stirred at room temperature overnight and concentrated at reduced pressure. 50 ml of ethyl acetate and 0.6 ml of triethylamine were added to the resulting residue, and the solution was stirred while cooling below −10° C.; 15 ml of ethyl acetate solution containing 0.95 ml (10.0 mmol) of ethyl chloroformate was added while maintaining the temperature at −13° C. to −17° C. 30 minutes later, 15 ml of ethyl acetate solution containing 2.38 g (9.51 mmol) of D-valine-N-(R)-α-methoxymethylbenzylamide was added to the solution while maintaining the temperature at −13° C. to −17° C. The solution temperature was raised to the room temperature and the mixture was filtered to remove precipitated dicyclohexylamine hydrochloride. 25 ml of 1N HCl was added to the filtrate, and the mixture was stirred at the room temperature for one hour and concentrated. 80 ml of acetic acid was added to the syrup-like residue, and 0.75 g of 10% Pd-C was added, and the mixture was stirred under hydrogen atomosphere for three days for catalytic reduction. The mother liquor, after catalyst removal by filtering, was HPLC analyzed and measured 1.83 g (5.01 mmol) of α-L-aspartyl-D-valine-N-(R)-α-methoxymethylbenzylamide. The yield was 52.7%.

Example 9

2.00 g (19.4 mmol) of D-α-aminobutyric acid, 2.25 g (19.4 mmol) of methyl acetoacetate, and 3.52 g (19.4 mmol) of dicyclohexylamine were added to 17 ml of methanol and was refluxed while heating for three hours and the mixture was concentrated at reduced pressure. 60 ml of ethyl acetate and 0.20 g (1.9 mmol) of N-methylmorpholine were added, the mixture was stirred while cooling (Solution IX); 20 ml of ethyl acetate solution containing 2.55 ml (19.4 mmol) of isobutyl chloroformate was added to Solution IX while maintaining the temperature at −15° C. to −17° C. 20 minutes later, 30 ml of ethyl acetate solution containing 2.37 g (15.7 mmol) of (S)-α-ethyl-p-hydroxybenzylamine was added at the same temperature. The solution was warmed to the room temperature and filtered to remove precipitated dicyclohexylamine hydrochloride. 30 ml of 1N HCl was added to the filtrate and stirred for ninety minutes at room temperature, and then separated into layers. The resulting aqueous layer was adjusted to pH11 with 1N NaOH, and then was extracted with approximately 70 ml of ethyl acetate.

The resulting ethyl acetate layer was dried over anhydrous magnesium sulfate, which was filtered later; the filtrate was concentrated at reduced pressure and dried. 2.72 g (11.5 mmol) of D-α-aminobutyric acid-N-(S)-α-ethyl-p-hydroxy benzylamide was measured as clear light yellow syrup. The yield was 73.2%.

2.74 g (14.9 mmol) of L-aspartic acid β-methyl ester hydrochloride, 1.73 g (14.9 mmol) of methyl acetoacetate and 5.41 g (29.8 mmol) of dicyclohexylamine were added to 25 ml of methanol; the mixture was refluxed while heating for three hours, and then concentrated at reduced pressure. Ethyl acetate was added to the resulting residue and the mixture was filtered to remove precipitated dicyclohexylamine hydrochloride. The filtrate was concentrated and then the syrup-like residue was obtained. 45 ml of ethyl acetate and 0.75 g (7.5 mmol) of N-methylmorpholine were added and cooled as described above, and ethyl acetate solution containing 1.96 ml (14.9 mmol) of isobutyl chloroformate was added. 20 minute later, the solution made by dissolving 2.67 g (11.3 mmol) of said D-α-aminobutyric acid-N-(S)-α-ethyl-p-hydroxybenzylamide into 30 ml of ethyl acetate was added to the mixture. The solution was warmed to the room temperature and ethyl acetate was distilled off by concentrating the solution at reduced pressure.

Acetonitrile and 200 ml of 2N HCl were added to the residue and heated at 60° C. for ten hours. The solution was HPLC analyzed and measured 2.94 g (8.37 mmol) of α-L-aspartyl D-α-aminobutyric acid-N-(S)-α-ethyl-p-hydroxybenzylamide. The yield was 74.1%.

The hydrolyzed solution was adjusted to pH6 with 25% NaOH and concentrated under reduced pressure; the resulting slurry was ice cooled and filtered at reduced pressure. The resulting α-L-aspartyl-D-α-amino butyric acid-N-(S)-α-ethyl-p-hydroxybenzylamide crystals were rinsed with a small amount of water, ethyl acetate, and chloroform, and then dried under reduced pressure. The gained amount was 2.43 g. The crystallization yield was 82.7%.

Example 10

1.47 g (8.00 mmol) of L-aspartic acid β-methyl ester hydrochloride, 0.93 g (8.0 mmol) of methyl acetoacetate and 5.66 g (16.0 mmol) of trioctylamine were added to 25 ml of methanol, and refluxed while heating for three hours (Solution X); Solution X was concentrated at reduced pressure. 30 ml of ethyl acetate was added to the resulting syrup-like residue and stirred while cooling below ≦−10° C. 15 ml of ethyl acetate solution containing 0.77 ml (8.0 mmol) of ethyl chloroformate was added to the reaction mixture while maintaining the temperature at −11° C. to −12° C. 20 minutes later, 20 ml of ethyl acetate solution containing 1.07 g (6.67 mmol) of D-valine-N-(S)-α-ethyl-p-hydroxybenzylamide was added while maintaining the temperature at −13° C. to 17° C. The solution was warmed to the room temperature, and 25 ml of 1N HCl was added to the solution and stirred at the room temperature for one hour. After the solution was separated into layers, the ethyl acetate layer was extracted twice with diluted hydrochloric acid. The aqueous layer was concentrated and 15 ml of 2N HCl was added to the residue, and heated at 60° C. for five hours. The hydrolyzed solution was HPLC analyzed and measured 1.70 g (4.66 mmol) of α-L-aspartyl-D-valine-N-(S)-α-ethyl-p-hydroxybenzylamide. The yield was 69.9%.

The hydrolyzed solution was adjusted to pH6 with 25% NaOH; the resulting slurry was stirred at 5° C. overnight and filtered under reduced pressure. The resulting α-L-aspartyl-D-valine-N-(S)-α-ethyl-p-hydroxybenzylamide crystals were rinsed with a small amount of water and dried under reduced pressure. The gained amount was 1.51 g. The crystallization yield was 88.8%.

Example 11

2.00 g (17.1 mmol) of D-valine, 1.98 g (17.1 mmol) of methyl acetoacetate, 3.10 g (17.1 mmol) of dicyclohexylamine were added to 17 ml of methanol and refluxed while heating for three hours (Solution XI); Solution XI was concentrated at reduced pressure. 60 ml of ethyl acetate, 0.17 g (1.7 mmol) of N-methylmorpholine were added to the resulting residue and stirred while cooling; 20 ml of ethyl acetate solution containing 2.24 ml (17.1 mmol) of isobutyl chloroformate was added to the mixture while maintaining the temperature at −15° C. to −17° C. 20 minutes later, 30 ml of ethyl acetate solution containing 2.34 g (13.8 mmol) of (S)-α-ethyl-p-chlorobenzylamine was added to the mixture at the same temperature. The solution was warmed to room temperature and filtered to remove precipitated dicyclohexylamine hydrochloride. 30 ml of 1N HCl was added to the filtrate and the solution was stirred at the room temperature for 90 minutes and then separated into layers. The resulting aqueous layer was adjusted to pH11 with 1N NaOH and extracted with approximately 60 ml of ethyl acetate. The resulting ethyl acetate layer was dried over anhydrous magnesium sulfate and filtered to remove magnesium sulfate; the filtrate was concentrated at reduced temperature and dried, and then 3.14 g (11.7 mmol) of D-valine-N-(S)-α-ethyl-p-chlorobenzylamide of a clear light yellow syrup-like was measured. The yield was 84.8%.

2.41 g (13.1 mmol) of L-aspartic acid β-methyl ester hydrochloride, 1.52 g (13.1 mmol) of methyl acetoacetate, and 4.75 g (26.2 mmol) of dicyclohexylamine were added to 25 ml of methanol, refluxed while heating for three hours, and then concentrated at reduced pressure. Ethyl acetate was added to the resulting residue and then the mixture was to remove precipitated dicyclohexylamine hydrochloride. The filtrate was concentrated, and then a syrup-like residue was obtained. 40 ml of ethyl acetate and 0.66 g (6.6 mmol) of N-methylmorpholine were added to the residue and cooled as described above, then 1.72 ml (13.1 mmol) of isobutyl chloroformate was added. 20 minutes later, the solution made by dissolving 3.01 g (11.2 mmol) of D-valine-N-(S)-α-ethyl-p-chlorobenzylamide into 25 ml of ethyl acetate, was added to the mixture. The resulting solution was warmed to the room temperature and ethyl acetate was distilled off by concentrating the reaction solution under reduced pressure. Acetonitrile and 200 ml of 2N HCl were added to the residue and heated at 60° C. for nine hours. The solution was HPLC analyzed and measured 3.44 g (8.98 mmol) of α-L-aspartyl-D-valine-N-(S)-α-ethyl-p-chlorobenzyl amide. The yield was 80.2%.

The hydrolyzed solution was adjusted to pH6 with 25% NaOH and was concentrated under reduced pressure; the resulting slurry was ice cooled, and filtered at reduced pressure. The resulting α-L-aspartyl-D-valine-N-(S)-α-ethyl-p-chlorobenzyl amide crystals were rinsed with a small amount of water, ethyl acetate and chloroform, and then dried at reduced pressure. The gained amount was 2.95 g. The crystallization yield was 85.8%.

Example 12

2.00 g (19.4 mmol) of D-α-aminobutyric acid, 2.25 g (19.4 mmol) of methyl acetoacetate and 3.52 g (19.4 mmol) of dicyclohexylamine were added to 17 ml of methanol (Solution XII); Solution XII was refluxed while heating for three hours and concentrated at reduced pressure. 60 ml of ethyl acetate and 0.20 g (1.9 mmol) of N-methylmorpholine were added to the resulting residue, and stirred while cooling; 20 ml of ethyl acetate solution containing 2.55 ml (19.4 mmol) of isobutyl chloroformate was added to the reaction solution while maintaining the temperature at −15° C. to −17° C.

20 minutes later, 30 ml of ethyl acetate solution containing 2.71 g (16.2 mmol) of (R)-α-methoxymethyl-p-hydroxybenzyl amine was added to the solution while maintaining the same temperature. The solution was warmed to the room temperature and filtered to remove precipitated dicyclohexylamine hydrochloride. 30 ml of 1N HCl was added to the filtrate and stirred at the room temperature for ninety minutes. The aqueous layer was adjusted to pH11 with 1N NaOH, and was extracted with approximately 70 ml of ethyl acetate. The resulting ethyl acetate layer was dried over anhydrous magnesium sulfate; magnesium sulfate was filtered; the filtrate was concentrated under reduced pressures and measured 3.08 g (12.2 mmol) of D-α-aminobutyric acid-N-(R)-α-methoxymethyl-p-hydroxybenzylamide as clear light yellow syrup. The yield was 75.3%.

2.74 g (14.9 mmol) of L-aspartic acid β-methyl ester hydrochloride, 1.73 g (14.9 mmol) of methyl acetoacetate 5.41 g (29.8 mmol) of dicyclohexylamine were added to 25 ml of methanol, and refluxed while heating for three hours, and then concentrated at reduced pressure. Ethyl acetate was added to the resulting residue and then the mixture was filtered to remove precipitated dicyclohexylamine hydrochloride. The filtrate was concentrated and it was obtained a syrup-like residue. 45 ml of ethyl acetate and 0.75 g (7.5 mmol) of N-methylmorpholine were added to the residue, and the solution was cooled as described above; then ethyl acetate solution containing 1.96 ml (14.9 mmol) of isobutyl chloroformate was added. 20 minutes later, the solution made by dissolving 2.98 g (11.8 mmol) of said D-α-aminobutyric acid-N-(R)-α-methoxymethyl-p-hydroxybenzyl amide into 30 ml of ethyl acetate was added to the mixture. The solution was warmed to the room temperature, the reaction solution was concentrated under reduced pressure and the ethyl acetate distilled off. Some acetonitrile and 200 ml of 2N HCl were added to the solution, and heated at 60° C. for six hours. The resulting mixture was HPLC analyzed and measured 3.38 g (9.19 mmol) of α-L-aspartyl-D-α-aminobutyric acid-N-(R)-α-methoxymethyl-p-hydroxybenzylamide. The yield was 77.9%. This hydrolyzed solution was adjusted to pH6 with 25% NaOH and concentrated under reduced pressure; the resulting slurry was ice cooled, and filtered at reduced pressure. The resulting α-L-aparthyl-D-aminobutyric acid-N-(R)-α-methoxymethyl-p-hydroxybenzylamide crystals were rinsed with a small amount of water, ethyl acetate and chloroform and dried at reduced pressure. The gained amount was 3.03 g. The crystallization yield was 89.6%.

Example 13

1.50 g (8.17 mmol) of L-aspartic acid β-methyl ester hydrochloride, 0.95 g (8.2 mmol) of methyl acetoacetate and 5.78 g (16.3 mmol) of trioctylamine were added to 25 ml of methanol (Solution XIII); Solution XIII was refluxed while heating for three hours and concentrated under reduced pressure. 30 ml of ethyl acetate was added to the syrup-like residue and stirred while cooling below −10° C., and 15 ml of ethyl acetate solution containing 0.79 ml (8.2 mmol) of ethyl chloroformate was added to the mixture while maintaining the temperature at −11° C. to −12° C. 20 minutes later, 20 ml of ethyl acetate solution containing 1.84 g (6.92 mmol) of D-valine-N-(R)-α-methoxymethyl-p-hydroxybenzylamide was added while maintaining the temperature at −13° C. to −17° C. The mixture was warmed to the room temperature, and 25 ml of 1N HCl was added to the reaction solution and stirred at the room temperature for one hour. After the solution was separated into layers, the ethyl acetate layer was extracted twice with diluted hydrochloric acid. The aqueous layer was concentrated, and 15 ml of 2N HCl was added to the resulting residue and heated at 60° C. for five hours. The hydrolyzed solution was HPLC analyzed and measured 1.92 g (5.02 mmol) of α-L-aspartyl-D-valine-N-(R)-α-methoxymethyl-p-hydroxybenzylamine. The yield was 72.5%.

The hydrolyzed solution was adjusted to pH6 with 25% NaOH, and the resulting slurry was stirred at 5° C. overnight, then filtered under reduced pressure. The resulting α-L-aspartyl-D-valine-N-(R)-α-methoxymethyl-p-hydroxybenzylamide crystals were rinsed with a small amount of water and dried at reduced pressure. The gained amount was 1.45 g. The crystallization yield was 75.5%.

As described above, present invention relates to producing α-L-aspartyldipeptide amide derivatives using economical protecting groups, activation agents and an easy process that does not yield β-peptide as a by-product. The invention can be used to produce sweetener compounds, the α-L-aspartyl-D-amino acid-N-(S)-α-alkylbenzylamide of U.S. Pat. No. 5,286,509, the aspartyldipeptide derivative of Japanese Patent Application No. 42818/1995, and the aspartyldipeptide amide derivatives of Japanese Patent Application No. 144844/1995 now pending as U.S. Ser. No. 08/579.976 (Attorney Docket 10-767-0), all incorporated herein by reference.

This application is based on Japanese patent applications 327094/1994, filed Dec. 28, 1994, and 215940/1995 filed Aug. 24, 1995, both incorporated herein by reference.

In one aspect of the invention the amino group of an L-aspartic acid β-alkylester is protected with acetoacetate or β-diketone. The resulting compound is converted into a mixed anhydride using an alkyl chloroformate, condensed with an amino acid amide derivative and then hydrolyzed under acidic conditions to effect deprotection of the amino protective group and conversion of ester moiety into a carboxylic acid, whereby the target α-L-aspartyldipeptide amide derivatives are obtained.

What is claimed as new and desired to be secured by Letters Patent of the United States is:

1. A process for producing α-L-aspartyldipeptide amide derivatives, which comprises the steps of:
   (a) preparing an L-aspartic acid derivative of formula (1) by reacting
      (i) an L-aspartic acid β-alkyl ester;
      (ii) a base; and
      (iii) a β-diketone or an acetoacetic acid ester;

wherein $R_1$ is an alkyl or alkoxy group with 1 to 4 carbon atoms or an aromatic group with 6 to 10 carbon atoms; $R_2$ is an alkyl group with 1 to 4 carbon atoms or an aromatic group with 6 to 10 carbon atoms; $R_3$ is an alkyl group with 1 to 4 carbon atoms or a benzyl group; and A is a protonated tertiaryamine, a dicyclohexylamine, or an alkaline metal;

(b) mixing the L-aspartic acid derivative of formula (1) with alkyl chloroformate and with an amino acid amide derivative of formula (2):

wherein $R_4$ is an alkyl group with 1 to 6 carbon atoms or an alkoxymethyl group with 2 to 7 carbon atoms; $R_5$ is a benzyl group, a cyclohexyl group, a cyclohexylmethyl group, a phenyl group, or a phenyl group with a substituent in its 2-, 3- or 4-position selected from F, Cl, Br, I, a hydroxyl group, an alkoxy group with 1 to 6 carbon atoms, a cyano group, a nitro group, an acetyl group, an amino group, an acetylamino group, or $R_5$ is a phenyl group with a methylenedioxy group, a trimethylene group, or a tetramethylene group in its 2, 3 or 3,4-position, or $R_5$ is a 2-, 3- or 4-pyridyl group, a 2- or 3-furyl group, or a 2- or 3-thienyl group; when $R_4$ is an alkylkoxymethyl group the configuration of C* is (R), (S), or (RS);

when $R_4$ is an alkyl group and $R_5$ is a benzyl group, a cyclohexyl group, a cyclohexylmethyl group, or a phenyl group X is a D-α-amino acid residue or a DL-α-amino alloisoleucine, D-threonine, D-0-methylthreonine, D-allothreonine, D-0-methylallothreonine, D- or DL-furylglycine, or a cyclic or non-cyclic, α,α-dialkyl amino acid residue with 3 to 6 carbon atoms; when 1) $R_4$ is an alkyl group and $R_5$ is a phenyl group with a substituent in its 2-, 3- or 4-position selected from the group consisting of F, Cl, Br, I, hydroxyl group, alkoxy group with 1 to 6 carbon atoms, cyano group, nitro group, acetyl group, amino group, acetylamino group, or a phenyl group with methylenedioxy, trimethylene or tetramethylene groups in its 2, 3- or 3,4-position, or 2-, 3- or a 4-pyridyl group, a 2- or 3-furyl group or a 2- or 3-thienyl group or 2) $R_5$ is an alkoxymethyl group X is a D-α-amino acid residue or a DL-α-amino acid residue selected from the group consisting of D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-phenylglycine, D- or DL-furylglycine, or a cyclic or non-cyclic α,α-dialkylamine acid residue with 3 to 6 carbon atoms;

and wherein L-Asp and x are α-bonded; and
   (c) hydrolyzing the resulting product under acidic conditions.

2. The process of claim 1, wherein the amino acid amide derivative is in an organic layer obtained by mixing and reacting an amino acid derivative of formula (3) with an alkyl chloroformate, mixing and reacting the resulting compound with the amine derivative of formula (4), contacting the resulting product with acidic water to obtain an aqueous solution containing an amino acid amide derivative and extracting with an organic solvent under alkaline conditions:

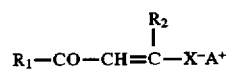

wherein $R_1$ is an alkyl or alkoxy group with 1 to 4 carbon atoms, or an aromatic group with 6 to 10 carbon atoms; $R_2$ is an alkyl group with 1 to 4 carbon atoms or an aromatic group with 6 to 10 carbon atoms; X is a D-α-amino acid residue or a DL-α-amino acid residue selected from the group consisting of D-alanine, D-α-amino butyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine or D-phenylglycine or D-or DL-furylglycine, or a cyclic or noncyclic α,α-dialkyl amino acid residue with 3 to 6 carbon atoms; A represents a protonated tertiaryamine, dicyclohexylamine, or an alkaline metal:

wherein $R_4$ is an alkyl group with 1 to 6 carbon atoms or an alkoxymethyl group with 2 to 7 carbon atoms; $R_5$ is a benzyl group, a cyclohexyl group, a cyclohexylmethyl group, a phenyl group, or a phenyl group with a substituent in its 2-, 3- or 4-position selected from the group consisting of F, Cl, Br, I, a hydroxyl group, an alkoxy group with 1 to 6 carbon atoms, a cyano group, a nitro group, an acetyl group, an amino group, an acetylamino group, or $R_5$ is a phenyl group with a methylenedioxy group, a trimethylene group, a tetramethylene group in its 2, 3- or 3,4-position, or $R_5$ is a 2-, 3- or 4-pyridyl group, a 2- or 3-furyl group, or a 2- or 3-thienyl group; when $R_4$ is an alkyl group the configuration of C* is (S) or (RS); when $R_4$ is an alkoxymethyl group the configuration of C* is (R), (S), or (RS).

3. The process of claim 1, wherein the base is a tertiary amine, secondary amine or inorganic base.

4. The process of claim 3, wherein the tertiary amine is triethylamine, tributylamine, trioctylamine or N-methylmorpholine.

5. The process of claim 3, wherein the secondary amine is dicyclohexylamine.

6. The process of claim 3, wherein the inorganic base is an alkaline metal.

7. The process of claim 6, wherein the alkaline metal is sodium hydroxide, potassium hydroxide or sodium carbonate.

8. The process of claim 1, wherein the acetoacetic acid ester is methyl acetoacetate or ethyl acetoacetate.

9. The process of claim 1, wherein the β-diketone is acetylacetone or benzoylacetone.

* * * * *